(12) United States Patent  
Shields

(10) Patent No.: US 7,041,077 B2
(45) Date of Patent: May 9, 2006

(54) UVEOSCLERAL DRAINAGE DEVICE

(75) Inventor: Milton B. Shields, Hamden, CT (US)

(73) Assignee: Yale University, New Haven, CT (US)

( * ) Notice: Subject to any disclaimer, the term of this patent is extended or adjusted under 35 U.S.C. 154(b) by 378 days.

(21) Appl. No.: 10/624,882

(22) Filed: Jul. 21, 2003

(65) Prior Publication Data
US 2004/0015140 A1 Jan. 22, 2004

Related U.S. Application Data

(60) Provisional application No. 60/397,565, filed on Jul. 19, 2002.

(51) Int. Cl.
A61M 5/00 (2006.01)
A61M 31/00 (2006.01)
A61B 17/32 (2006.01)

(52) U.S. Cl. ............. 604/8; 604/93.01; 606/167; 606/172

(58) Field of Classification Search ......... 604/8–10, 604/30, 500, 43, 93.01, 289, 295; 606/4, 606/6, 107, 108, 161, 166, 167, 170, 172, 606/109; 623/4.1, 6.12
See application file for complete search history.

(56) References Cited

U.S. PATENT DOCUMENTS

| | | | |
|---|---|---|---|
| 4,099,529 A | 7/1978 | Peyman | 128/305 |
| 4,521,210 A | 6/1985 | Wong | 604/8 |
| 4,604,087 A | 8/1986 | Joseph | 604/9 |
| 4,750,901 A | 6/1988 | Molteno | 604/8 |
| 4,946,436 A | 8/1990 | Smith | 604/8 |
| 5,041,081 A | 8/1991 | Odrich | 604/9 |
| 5,171,213 A | 12/1992 | Price, Jr. | 604/9 |
| 5,342,370 A | 8/1994 | Simon et al. | 606/107 |
| 5,411,473 A | 5/1995 | Ahmed | 604/8 |
| 5,433,701 A | 7/1995 | Rubinstein | 604/8 |
| 5,454,796 A | 10/1995 | Krupin | 604/294 |
| 5,476,445 A | 12/1995 | Baerveldt et al. | 604/8 |
| 5,558,630 A | 9/1996 | Fisher | 604/8 |
| 5,573,544 A | 11/1996 | Simon et al. | 606/151 |
| 5,601,094 A | 2/1997 | Reiss | 128/899 |
| 5,676,679 A | 10/1997 | Simon et al. | 606/170 |
| 5,704,907 A | 1/1998 | Nordquist et al. | 604/8 |
| 5,879,319 A | 3/1999 | Pynson et al. | 604/8 |
| 5,882,327 A | 3/1999 | Jacob | 604/8 |
| 6,007,510 A | 12/1999 | Nigam | 604/8 |
| 6,077,299 A | 6/2000 | Adelberg et al. | 623/24 |
| 6,102,045 A | 8/2000 | Nordquist et al. | 128/898 |
| 6,142,969 A * | 11/2000 | Nigam | 604/8 |
| 6,186,974 B1 | 2/2001 | Allan et al. | 604/30 |
| 6,383,219 B1 | 5/2002 | Telandro et al. | 623/4.1 |
| 6,589,203 B1 | 7/2003 | Mitrev | 604/27 |

* cited by examiner

Primary Examiner—Patricia Bianco
Assistant Examiner—Leslie R. Deak
(74) Attorney, Agent, or Firm—Needle & Rosenberg, P.C.

(57) ABSTRACT

An ophthalmic shunt implantable in an eye having an elongate body and a conduit for conducting aqueous humor from an anterior chamber of the eye to the suprachoroidal space of the eye. The elongate body has a forward end and an insertion head that extends from the forward end. The insertion head defines a shearing edge suitable for cutting eye tissue engage thereby. The forward end and the insertion head of the body define a shoulder surface. The conduit has a first end defined on a portion of a top surface of the insertion head. The conduit also extends through the body from the forward end to a back end thereof. The first end of the conduit is spaced from the shearing edge and, in one example, from the shoulder of the body.

84 Claims, 7 Drawing Sheets

CYCLODIALYSIS; ENHANCED UVEOSCLERAL FLOW

CYCLODIALYSIS; SPATULA INSERTION

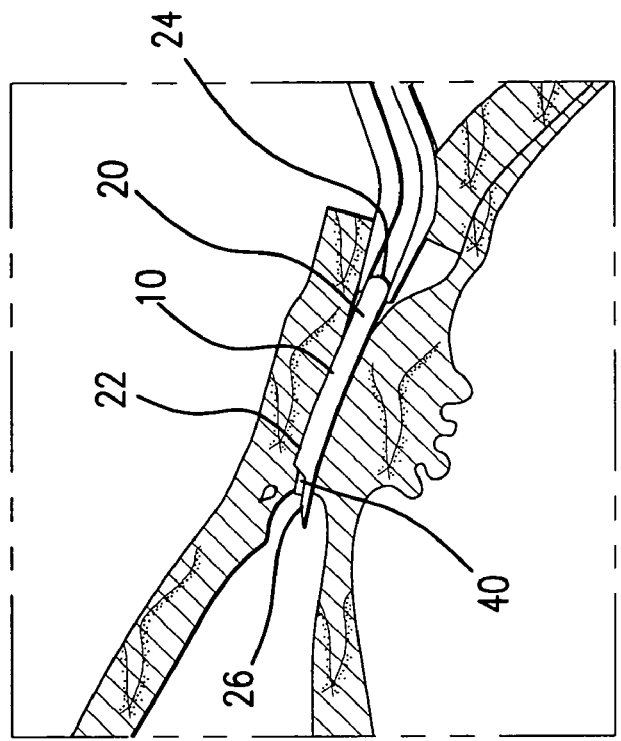
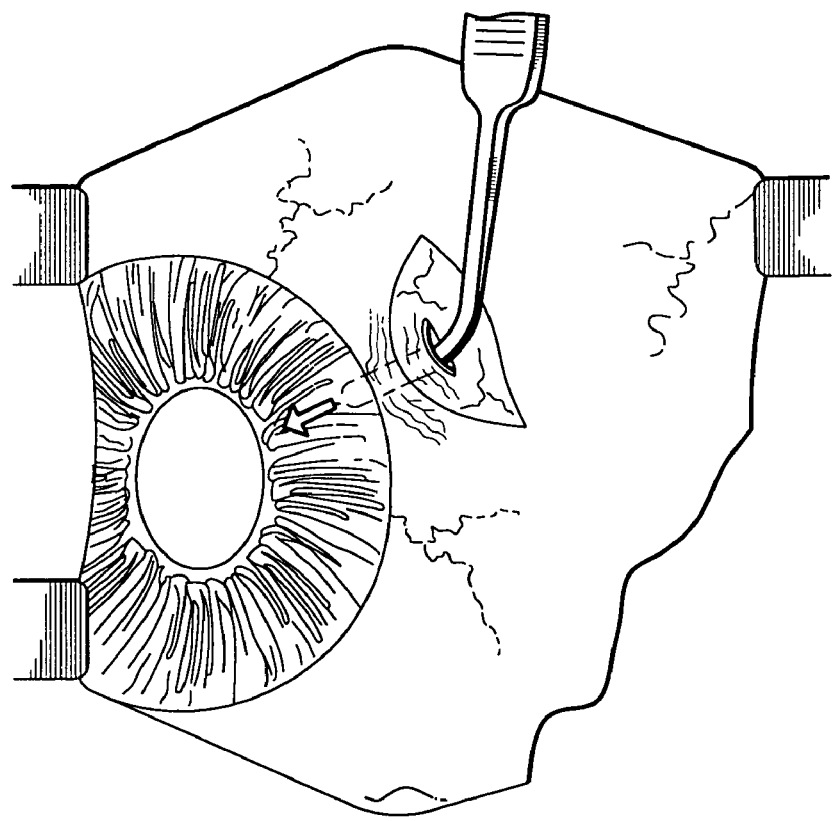

UVEOSCLERAL DRAINAGE DEVICE

This application claims the benefit of Provisional Application No. 60/397,565, filed Jul. 19, 2002.

FIELD OF THE INVENTION

The invention relates to eye implants, more particularly, to an ophthalmic shunt and method of using same for use in enhancing uveoscleral drainage in the eye to lower eye pressure.

BACKGROUND OF THE INVENTION

Glaucoma, a leading cause of world blindness, is a group of disorders, characterized by irreversible damage to the optic nerve, or glaucomatous optic neuropathy, in which elevated intraocular pressure is the main causative risk factor. The only proven way to prevent the blindness of glaucoma is to control the intraocular pressure.

Clinical management of intraocular pressure can be achieved medically or surgically. Modern medical therapy for glaucoma began in the 1870s, with the introduction of pilocarpine and other cholinergic agonists. In the twentieth century, several compounds were introduced, such as alpha-2 agonists, beta-adrenergic antagonists, topical and systemic carbonic anhydrase inhibitors, and prostaglandins. However, glaucoma medication are not available or practical in many parts of the world, and are inadequate in many patients, despite availability. Hence the need for surgical methods to control the intraocular pressure.

Control of intraocular pressure can be achieved surgically by reducing the production of aqueous humor or by increasing its outflow. Operations to reduce production, referred to collectively as cyclodestructive surgery, destroy a portion of the ciliary body, the source of aqueous humor. Destructive elements over the years have included diathermy, cryotherapy and, most recently, laser energy. While these operations are effective in lowering the intraocular pressure, and are beneficial in desperate cases, they have a high complication rate, including inflammation and further reduction in visual acuity.

Referring to FIG. 1, after production by the ciliary body, aqueous humor leaves the eye by many routes. Some goes posteriorly through the vitreous body to the retina, while most circulates in the anterior segment of the eye, nourishing avascular structures such as the lens and cornea, before outflow by two main routes: canalicular or uveoscleral.

The canalicular, also referred to as the trabecular or conventional, route is the main mechanism of outflow, accounting for approximately 80% of aqueous egress from the normal eye. The route is from the anterior chamber angle (formed by the iris and cornea), through the trabecular meshwork, into Schlemm's canal. The latter is a 360° channel just peripheral to meshwork. It is connected to intrascleral outlet channels that take the aqueous through the sclera to reunite with the blood stream in the episcleral veins.

The uveoscleral route is less clear with regard to anatomy and physiologic significance, but probably accounts for 10–20% of aqueous outflow in the normal human eye. As with the canalicular route, the uveoscleral pathway begins in the anterior chamber angle. The aqueous is absorbed by portions of the peripheral iris, the ciliary body and probably the trabecular meshwork, from whence it passes posteriorly through the longitudinal muscle of the ciliary body to the suprachoroidal space (between the choroids and sclera). Aqueous in the suprachoroidal space may pass as far posteriorly as the optic nerve and leave the eye through a variety of emissaria around nerves and vessels in the sclera.

A majority of operations that have been devised to enhance the aqueous outflow as a means of treating glaucoma have focused on enhancing canalicular outflow. The ideal glaucoma operation would be to re-establish normal canalicular flow into Schlemm's canal. In some forms of glaucoma this is possible, such as the iridectomy (introduced in the 1850s) for pupillary block glaucoma and goniotomy and trabeculotomy (introduced in the mid-twentieth century) for congenital glaucoma. For the vast majority of glaucomas, however, the obstruction to outflow (and, hence, the elevated intraocular pressure) is in the trabecular meshwork, and the only effective surgical approach has been to bypass the normal canalicular pathway and create bulk outflow by one of two methods: filtration surgery and drainage implant devices.

Filtration surgery was introduced in the first decade of the twentieth century. The basic principle is the creation of a fistula through trabecular meshwork, Schlemm's canal and sclera. Aqueous flows through the fistula to create a pool beneath the elevated conjunction (called a bleb), through which it filters to wash away in the tear film. The basic operation, in a variety of modified forms, has now been the preferred glaucoma procedure for nearly 100 years, despite serious limitations.

Limitations of filtering surgery include failure due to fibrotic closure of the fistula. Of even greater concern are the complications associated with excessive outflow, which include an intraocular pressure that is too low (hypotony) and a conjunctival filtering bleb that becomes too thin, with leakage and the risk of infection (endophthalmitis).

Drainage implant surgery was developed primarily to overcome the problem of fistula closure, since a conduit passes from the anterior chamber angle, through the fistula, to a plate beneath the conjuctiva. However, these operations are also complicated by early hypotony and late failure due to obstruction of the conduit or excessive fibrosis over the plate. There is a need, therefore, for a device and method of using same that reliably channels aqueous into pathways without creating hypotony or a filtering bleb.

Although the uveoscleral pathway may only account for 10–20% of aqueous outflow in the normal state, there is evidence that it can be enhanced to accommodate a significantly greater percentage of outflow. For example, topical prostaglandins, which work nearly exclusively by increasing uveoscleral outflow, can lower the intraocular pressure by 30–50% in some patients. Even more compelling are the results of early surgical attempts to enhance uveoscleral outflow.

In the first decade of the twentieth century, paralleling the introduction of filtering surgery, an operation was devised to enhance uveoscleral outflow, called cyclodialysis. Referring to FIGS. 2A and 2B, the basic principle is separation of the ciliary body from the scleral spur, which provides a direct route for aqueous flow from the anterior chamber angle to the suprachoroidal space. Unlike filtering surgery, however, cyclodialysis enjoyed only limited acceptance in the twentieth century. Although it was commonly used during the first half of the century, serious limitations led to its virtual abandonment by mid-century. The limitations were twofold. When so-called cyclodialysis cleft was patent, the operation often worked too well, with significant hypotony. In many patients, the cleft would close suddenly, with a profound rise in the intraocular pressure.

A variety of efforts have been made to prevent closure of the cleft by wedging flaps of ocular tissue or plastic devices into the space. To date, none of these techniques have proved success.

SUMMARY

The present invention relates to eye implant devices for lowering intraocular pressure in an eye. In one example, an ophthalmic shunt suitable for implantation in an eye is provided. In this example, the shunt has an elongate body and a conduit for conducting aqueous humor from an anterior chamber of the eye to the suprachoroidal space of the eye. The elongate body has a forward end and an insertion head that extends from the forward end. The insertion head defines a shearing edge suitable for cutting eye tissue engaged thereby. Together, the forward end and the insertion head of the body define a shoulder surface.

In one example, the elongate body may have a substantially fusiform cross-sectional shape. The elongate body may also have an arcuate shape along at least a portion of its length with a radius of curvature suitable for extending along the curvature of the sclera of the eye.

The conduit of the shunt has a first end defined on a portion of a top surface of the insertion head. The conduit also extends through the body from the forward end to a back end thereof. The first end of the conduit is spaced from both of the shearing edge and the shoulder of the body. The conduit may be formed of a porous wicking member suitable for regulating the flow of aqueous humor from a first end to a second end of the conduit. Alternatively, the wicking member may be disposed within at least a portion of the conduit.

The shunt may be readily implanted within the eye of a patient in order to reduce the intraocular pressure within the eye. In one example, a first incision in and through the conjunctiva and the sclera at a position posterior to the limbus is made. The shunt is then grasped by the surgeon with, for example, a surgical tool, whereupon the insertion head of the shunt is passed through the first incision and into the supraciliary space of the eye. Next, at least a portion of the shearing edge of the insertion head is inserted into and through the anterior chamber angle into the anterior chamber of the eye. When the insertion head is inserted within the anterior chamber, the first end of the conduit is placed in fluid communication with the anterior chamber and the second end of the conduit is placed in fluid communication with the suprachoroidal space. Thus, aqueous humor is allowed to flow from the anterior chamber of the eye to the suprachoroidal space, which allows the intraocular pressure in the eye to be lowered.

In use, the shunt prevents cleft closure and controls the rate of aqueous flow into the suprachoroidal space via the conduit, which prevents hypotony. Thus, the design of the present invention overcomes the limitations inherent in the traditional cyclodialysis procedure: hypotony and cleft closure.

DETAILED DESCRIPTION OF THE DRAWINGS

FIG. 6A is a partial top view of an eye having an implant, according to the present invention, being positioned into the anterior chamber of the eye.

FIG. 6B is an enlarged cross-sectional detail view of the implant of FIG. 6A.

DETAILED DESCRIPTION OF THE INVENTION

The present invention is more particularly described in the following examples that are intended as illustrative only since numerous modifications and variations therein will be apparent to those skilled in the art. Thus, the embodiments of this invention described and illustrated herein are not intended to be exhaustive or to limit the invention to the precise form disclosed. They are chosen to describe or to best explain the principles of the invention and its application and practical use to thereby enable others skilled in the art to best utilize the invention. As used in the specification and in the claims, "a," "an," and "the" can mean one or more, depending upon the context in which it is used. The preferred embodiment is now described with reference to the figures, in which like numbers indicate like parts throughout the figures and views.

Figure 1:
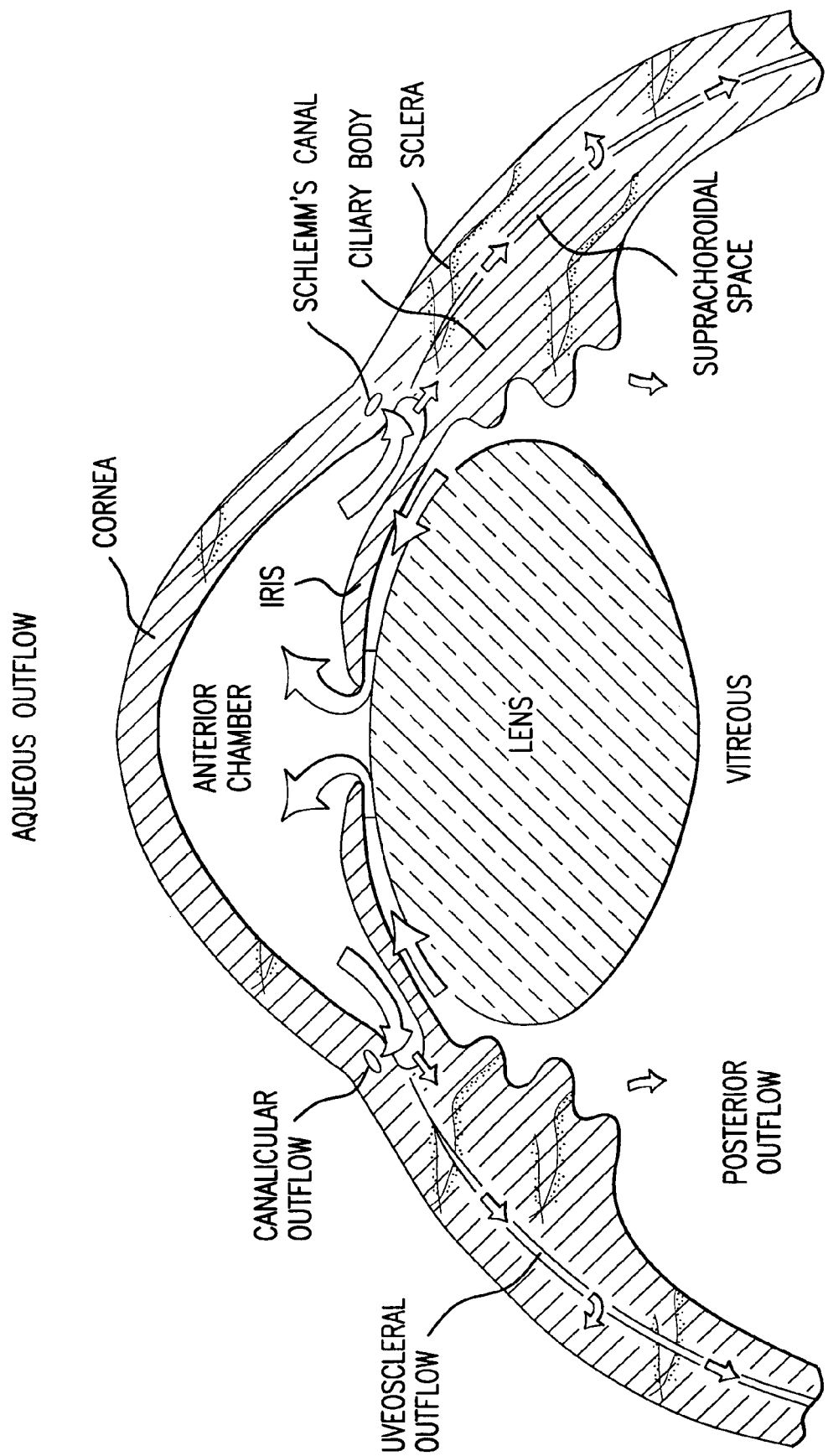
FIG. 1 is a partial cross-sectional view of an eye showing the normal aqueous flow of aqueous humor though the anterior chamber of the eye.
Figure 2B:
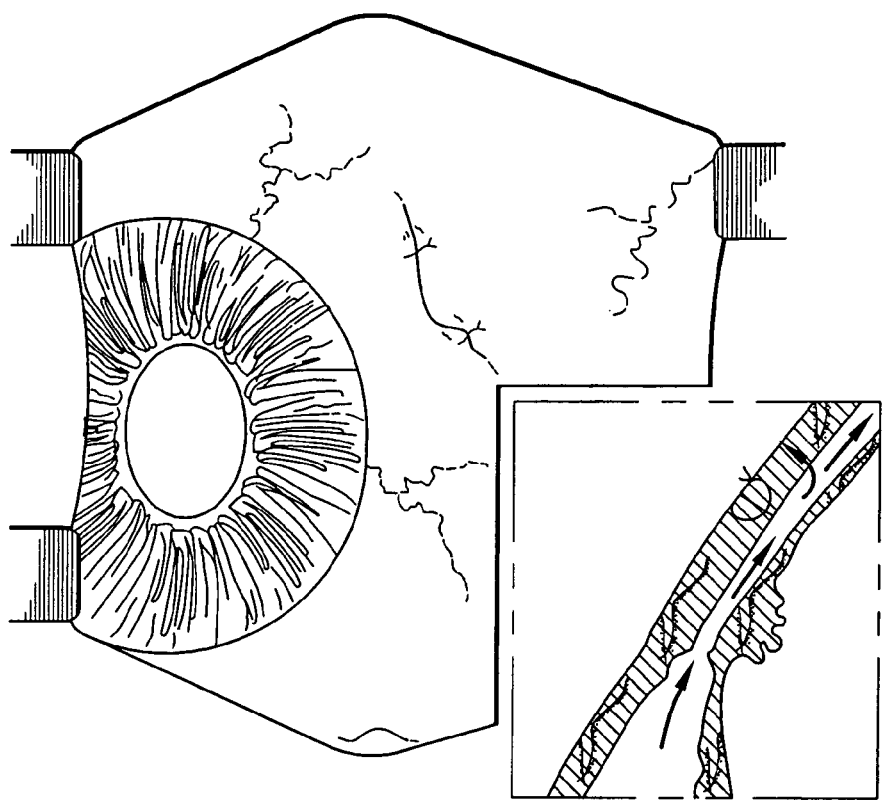
FIGS. 2A and 2B are partial top views of an eye showing the prior art cyclodialysis operation and the typical result.
Figure 2A:
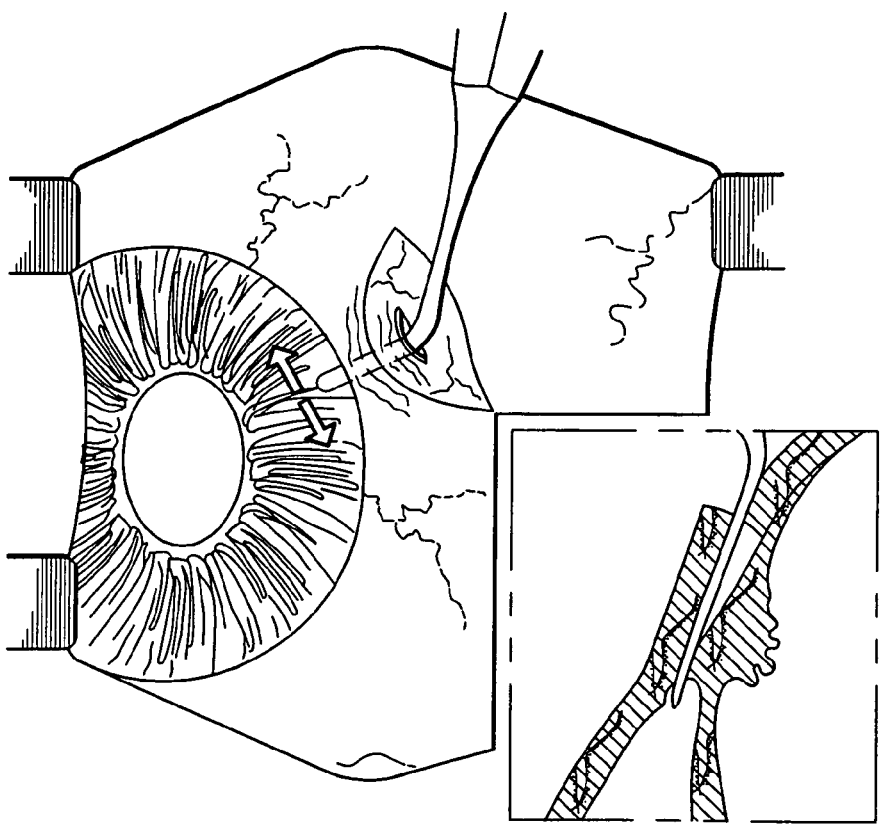
Figure 3A:
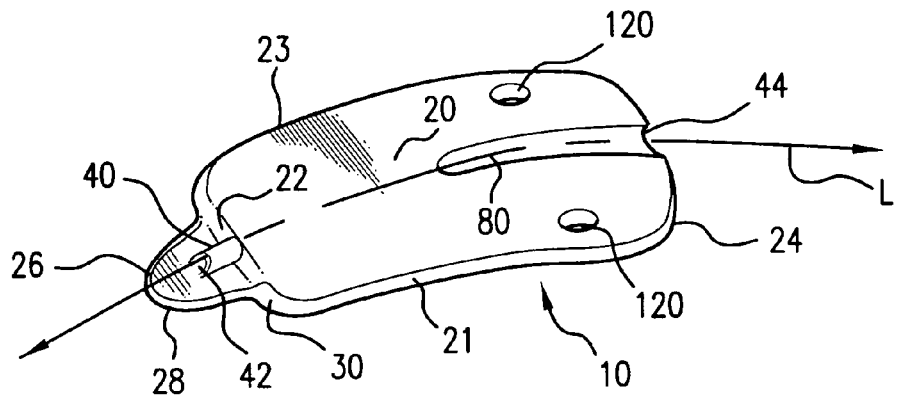
FIG. 3A is a perspective view of a first embodiment of the present invention.
Figure 3B:
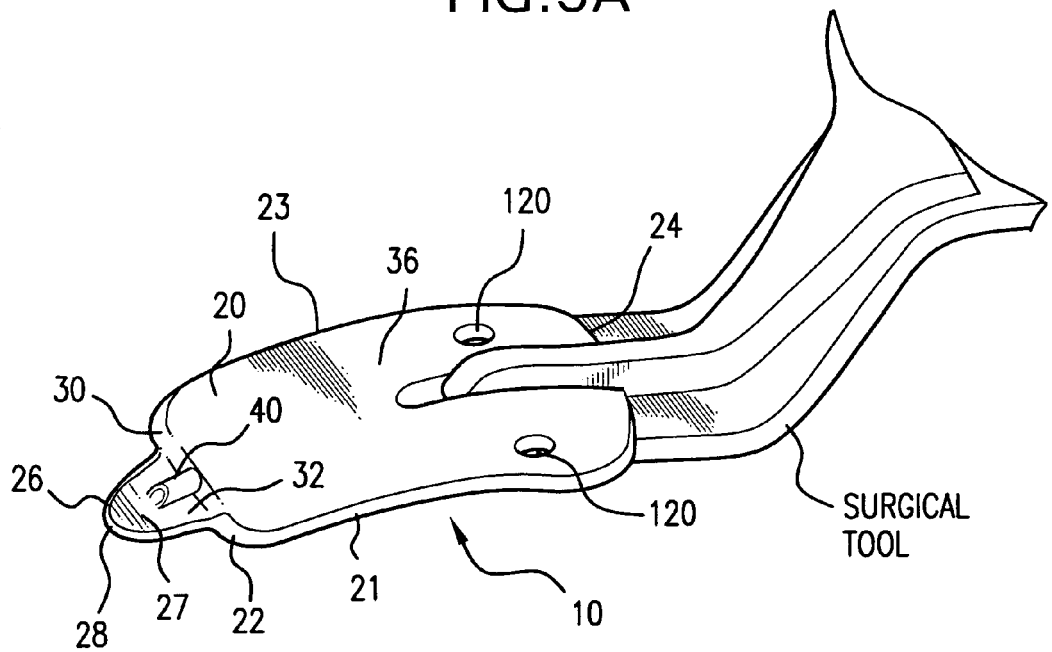
FIG. 3B is a perspective view of the embodiment shown in FIG. 3A being grasped by a surgical tool.
Figure 3C:
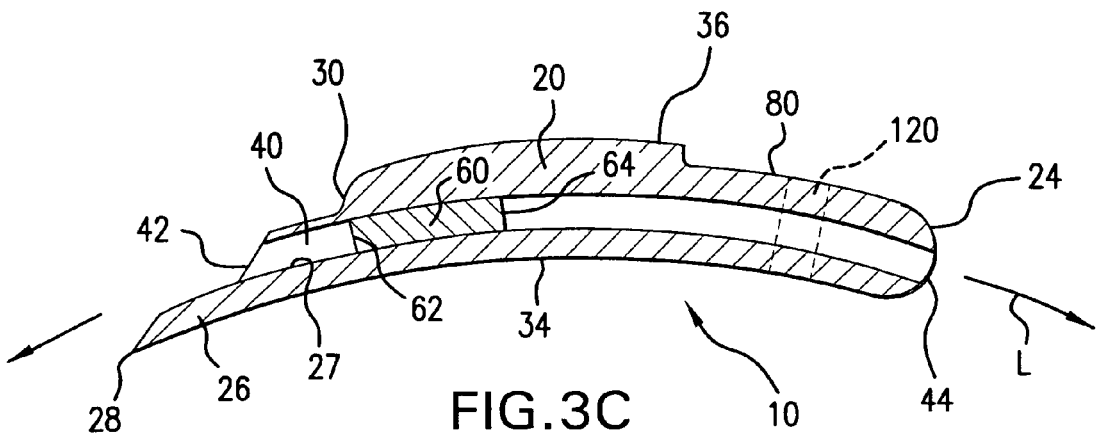
FIG. 3C is a cross-sectional view of the embodiment shown in FIG. 3A taken along line 3A.

Referring to FIGS. 3A–5D, examples of uveoscleral drainage devices of the present invention are shown. The implant or shunt 10 of the present invention comprises an uveoscleral drainage device that is adapted for implantation within an eye of a patient. Referring initially to FIGS. 3A–3C, the shunt 10 comprises an elongate body 20 and a conduit 40. The elongate body has a forward end 22, a spaced back end 24, and extends along a longitudinal axis L. The body also has an insertion head 26 that extends generally longitudinally from the forward end thereof. The elongate body further has a first elongate edge 21 and a second elongate edge 23 that extend respectively from the forward end to the back end of the body. The insertion head is adapted for insertion into the anterior chamber of the eye and defines a shearing edge 28 constructed and arranged for cutting eye tissue engaged thereby. In the example shown, the shearing edge of the insertion head may have an arcuate shape. However, as one skilled in the art will appreciate, other shapes, such as, for example, chisel shapes, scalpel shapes, and the like, are contemplated for the shearing edge.

The juncture of the insertion head 26 against the forward end 22 of the body defines a shoulder surface 30 thereon. In one example, the insertion head has a base portion 32 having a first width and where the respective first and second elongate edges are spaced apart a second width that is greater than the first width. The shoulder surface 30 of the body is adapted to engage tissue portions of the anterior chamber angle of the eye that are adjacent an interior surface of the interior chamber. The shoulder surface 30 also aids is limiting the anterior movement or displacement of the device when implanted, which helps prevent the forward end 22 of the drainage device from penetrating and entering the anterior chamber. In the example shown, the base portion of the insertion head 26 extends substantially co-planar to a lower surface 34 of the elongate body. Alternatively, the insertion head 26 may extend from a portion of the forward end that is spaced from the circumferential edge of the forward end. In this example, the shoulder surface 30 would extend about the periphery of the base portion of the insertion head.

The body 20 has a length from the forward end to the back end of such extent to extend from proximate the interior surface of the anterior chamber to the suprachoroidial space of the eye. The back end 24 of the body is adapted for insertion within the suprachoroidial space of the eye. Along at least a portion of its length, the body may be substantially planar or may have an arcuate shape that is adapted to extend along a portion of the curvature of the sclera of the eye. As one will appreciate from the illustrated embodiment, the body is generally thin to provide a less irritating fit within the eye.

In one example, the elongate body 20 has a substantially fusiform cross-sectional shape. This fusiform shape aids in stabilizing the device when implanted as tissues of the anterior chamber angle surround portions of the exterior surface of the body. A variety of cross-sectional shapes are contemplated for the elongate body as long as a shoulder surface is defined in the forward end.

The conduit 40 has a first end 42 and a spaced second end 44. In the example shown, a portion of the conduit is defined on a portion of a top surface 27 of the insertion head 26 with the remaining portion defined within the elongate body 20 and extending from the forward end to the back end thereof. The first end of the conduit is spaced from the shearing edge 28 and is spaced from the shoulder surface 30 of the body. In one example, the first end 42 of the conduit is positioned at an acute angle with respect to the top surface 27 of the insertion head. In the example shown in FIG. 3A, the conduit is formed integrally with the elongate body. One will appreciate however, and as shown in FIGS. 4A–4C, that the conduit 40 may also be a separate member which is connected to the elongate body.

Figure 4A:
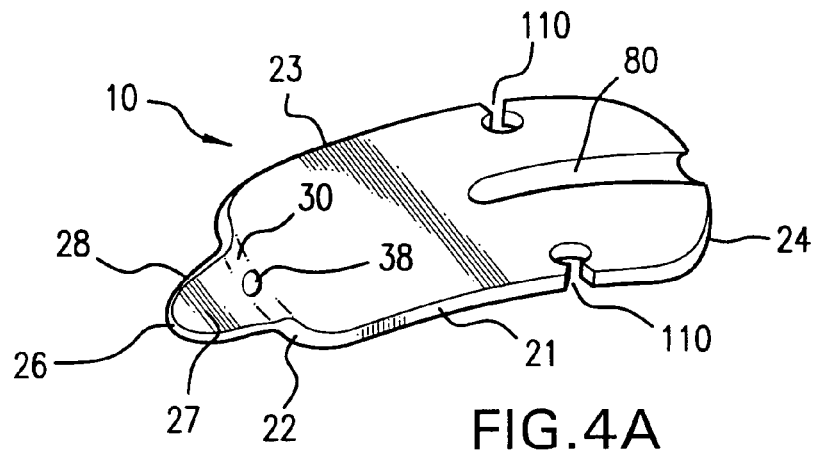
FIG. 4A is a perspective view of an elongate body of a second embodiment of the present invention.
Figure 4B:
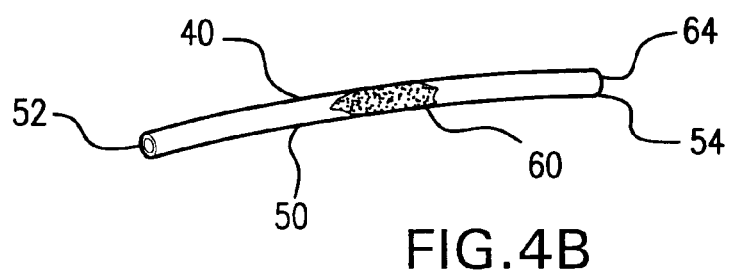
FIG. 4B is a perspective view of an elongate conduit of the second embodiment of the present invention.
Figure 4C:
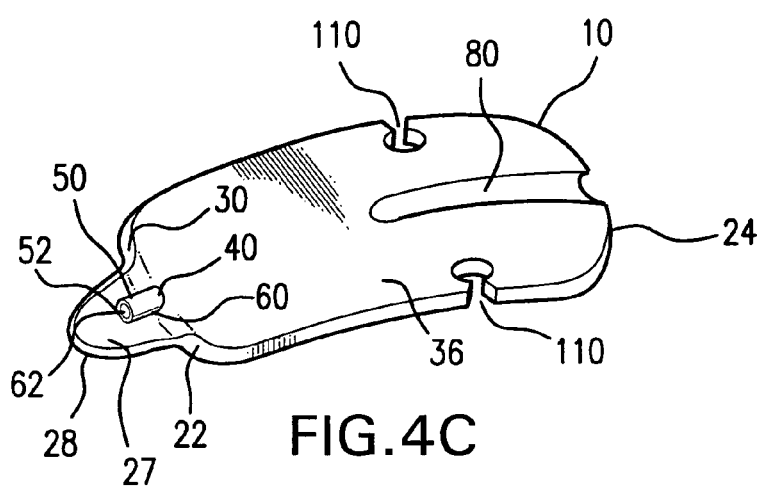
FIG. 4C is a perspective view of the second embodiment with the elongate conduit shown in FIG. 4B disposed within a portion of the elongate body and overlying a portion of a top surface of an insertion head.
Figure 4D:
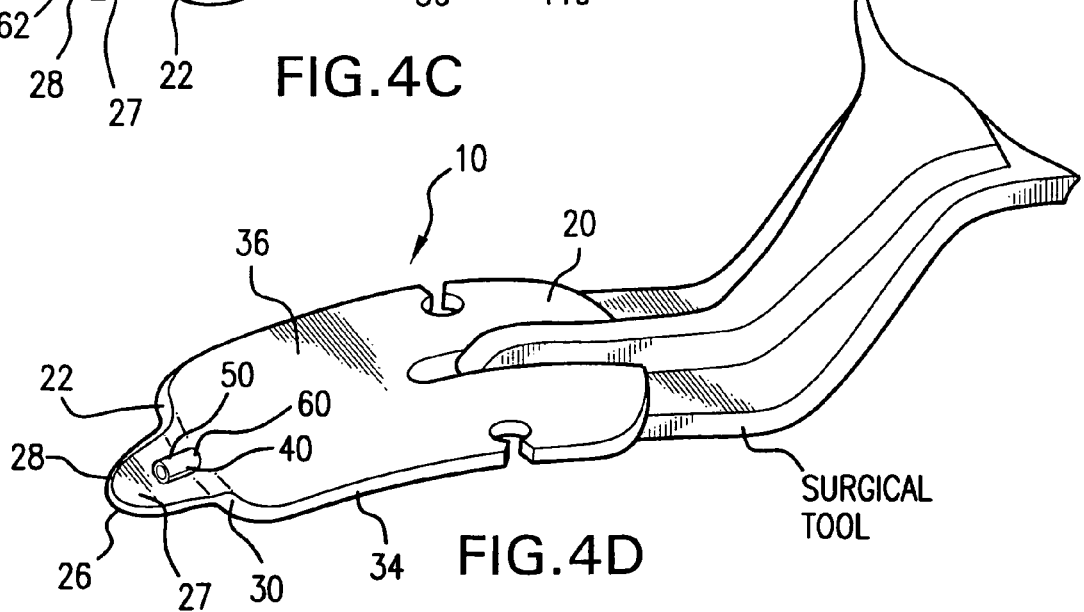
FIG. 4D is a perspective view of the second embodiment shown in FIG. 4C being grasped by a surgical tool.

Referring to FIGS. 4A to 4C, the conduit 40 of the present invention comprises an elongate tube 50 having a first end 52 and a spaced second end 54. Further, the elongate body defines a longitudinally extending bore 38 therein. A proximal end of the bore is defined in the forward end of the body and is positioned adjacent the top surface of the insertion head. In use, at least a portion of the tube is positioned within the bore of the body such that the second end 54 of the tube is positioned proximate a distal end of the bore. Further, the first end 52 of the tube extends through the proximal end of the bore and overlies a portion of the top surface 27 of the insertion head. In the example shown, the first end 52 of the tube is spaced from both the shearing edge and the shoulder surface of the body 20. As one will appreciate, the tube 50 positioned within the bore of the body forms the "conduit" 40 described in reference to FIGS. 3A–3C.

Referring to FIGS. 3A to 4C, the conduit may comprise a wicking member 60 that is constructed and arranged for regulating the flow of aqueous humor from an inlet end 62 to an outlet end 64 of the wicking member. This wicking member may, in one example, be a porous material suitable for insertion within at least a portion of the conduit. Such a wicking member 60 may be readily used in the embodiment shown in FIG. 3A. Alternatively, the wicking member 60 may be a porous material surrounded by a non-porous sheath. Such a sheathed wicking member could be used as the "tube" in the embodiment shown in FIGS. 4A–4C. Alternatively, the wicking member 60 could be formed from a plurality of tubular conduits. The flow rate through the wicking member may be controlled selectively choosing among the porosity of the material used, the length of the wicking member, and/or the number and relative size of the tubular conduits used in the respective examples. The use of a wicking member 60 allows for the variation of outflow required from the conduit to relieve undesired intraocular pressure. It is contemplated to provide implant devices of the present invention that would provide the desired aqueous humor flow to obtain a desired intraocular pressure. Thus, the physician can match the flow rate of the respective implant to the particular need of a patient. For example, versions of the device could be offered in various flow rates and/or pressure gradients.

Figure 5A:
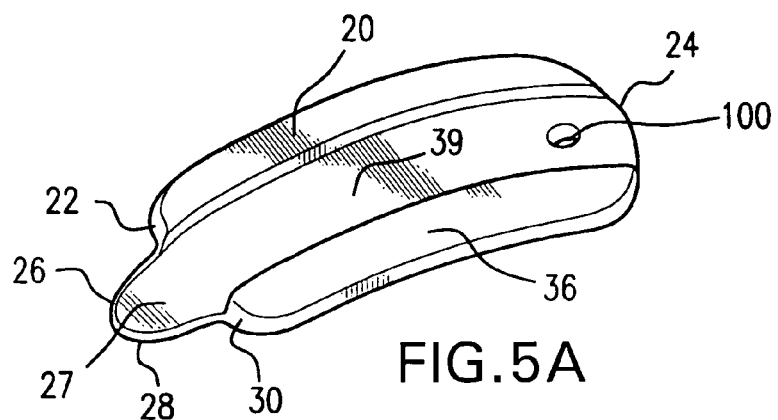
FIG. 5A is a perspective view of an elongate body of a third embodiment of the present invention.
Figure 5B:
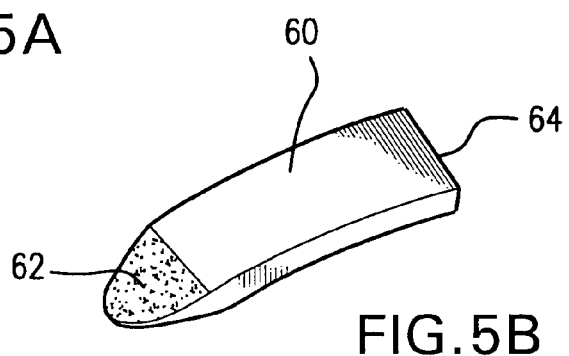
FIG. 5B is a perspective view of an elongate wicking member having an inlet end and an outlet end.
Figure 5C:
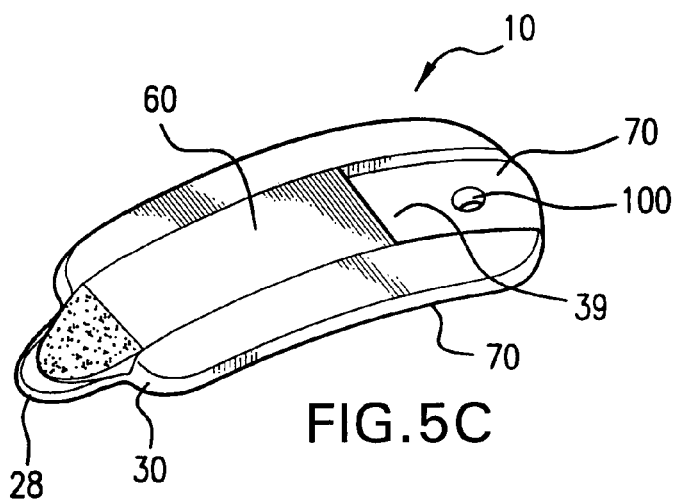
FIG. 5C is a perspective view of the third embodiment with the elongate wicking member shown in FIG. 5B disposed within a slit of the elongate body and overlying a portion of a top surface of an insertion head.
Figure 5D:
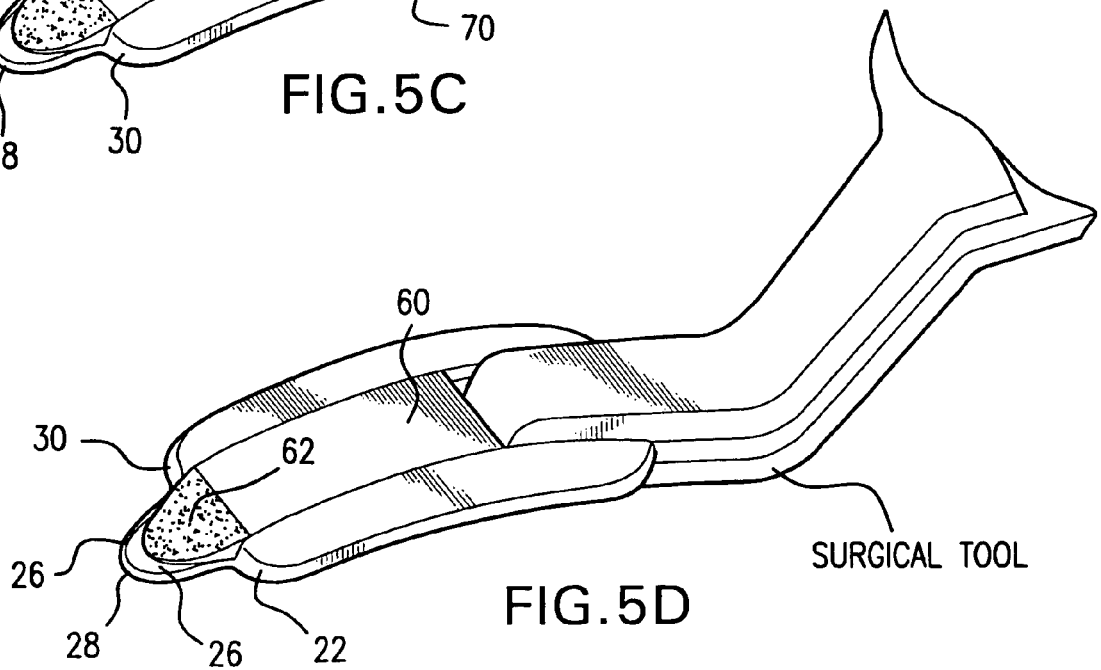
FIG. 5D is a perspective view of the third embodiment of FIG. 5C being grasped by a surgical tool.
Figure 7B:
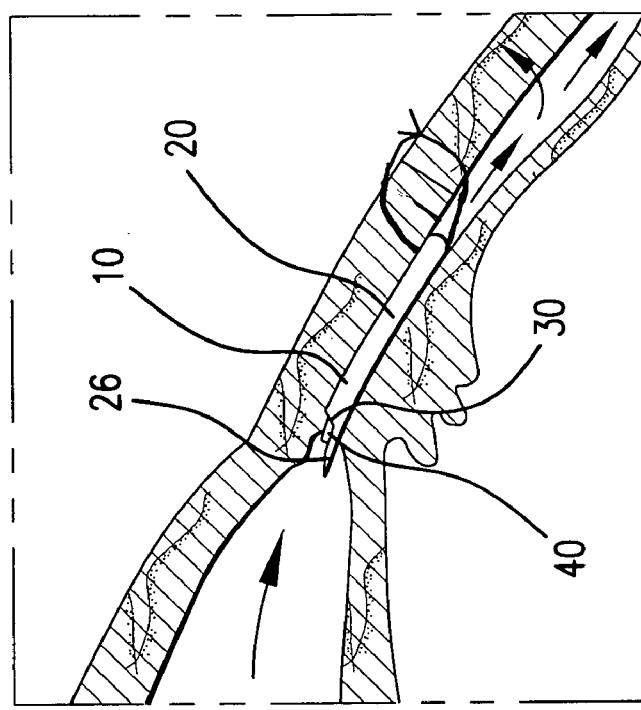
FIG. 7B is an enlarged cross-sectional detail view of the implant of FIG. 7A.
Figure 7A:
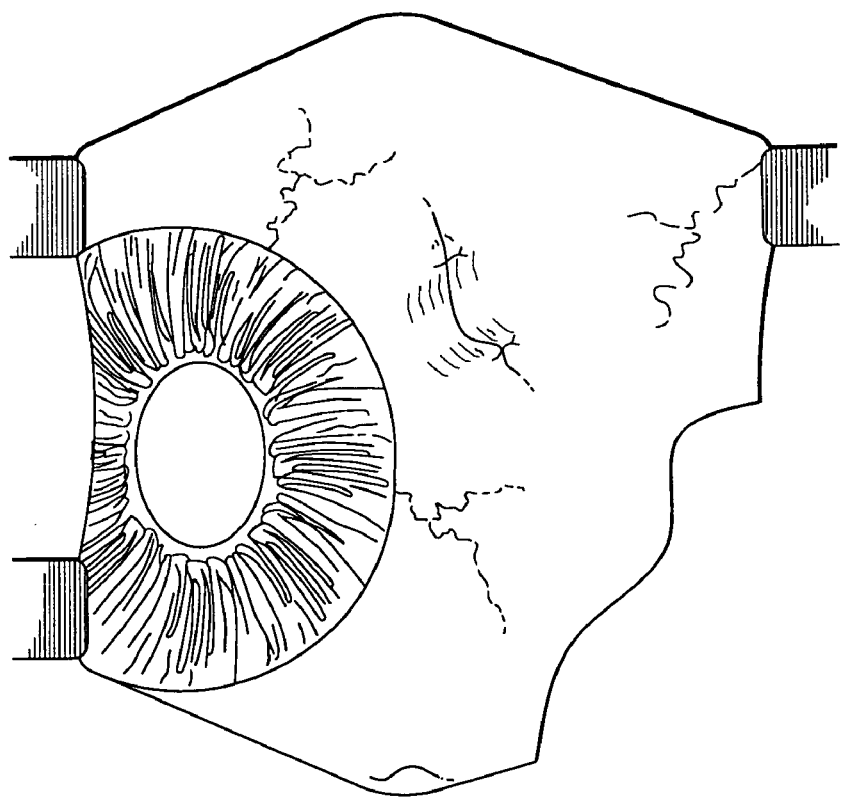
FIG. 7A is a partial top view of an eye in which an implant according to the present invention is located therein post-operatively.

Turning to FIGS. 5A–5C, an alternative embodiment of the device is shown that includes a wicking member 60. Here, an upper surface 36 of the elongate body defines a longitudinally extending slit 39. In one example, the slit extends from the forward end to the back end of the body. In this embodiment, the wicking member 60 is constructed and arranged so that the flow of aqueous humor from the inlet end 62 to the outlet end 64 is regulated and aqueous humor entering the inlet end can only exit the outlet end, which is placed in communication with the suprachoroidal space. The wicking member 60 is positioned within at least a portion of the slit of the body and overlies a portion of the top surface 27 of the insertion head 26. The inlet end 62 of the wicking member is spaced from the shearing edge of the body and, in one example, the inlet end is positioned at an acute angle with respect to the top surface of the insertion head.

Referring now to FIGS. 3A, 4C, and 5C, the elongate body provides a means for grasping the body by a surgical tool such as, for example, forceps and the like. In one example, as shown in FIG. 5C, at least one planar surface 70 constructed and arranged for grasping by the surgical tool is defined on at least a portion of at least one of the respective upper and lower surfaces of the elongate body. In this example, a portion of the slit in the elongate body forms one planar surface.

Alternatively, as shown in FIGS. 3A and 4C, the elongate body 20 may define a longitudinally extending groove 80, extending from the back end of the body, in the exterior surface of the body. The groove 80 is constructed and arranged for grasping by the surgical tool. One will appreciate that the groove may be positioned in the upper surface or in the lower surface of the body. Alternatively, a second longitudinally extending groove or a planar surface may be defined in the opposite spaced respective upper or lower surface to facilitate secure grasping of the device. As one will appreciate, any combination of planar surfaces and/or grooves on the respective upper and lower surfaces may be used to provide suitable grasping surfaces for the surgical tool.

After implantation the shunt may be fixed to a portion of the sclera of the eye. In the example shown in FIG. 5C, to facilitate fixation, the shunt may have at least one stitching loop 100 defined in the elongate body. Sutures can be passed through the loop and secured to the sclera. In the example shown in FIG. 3A, the elongate body has a pair of spaced notches 110 that are constructed and arranged for facilitating suturing of the elongate body to eye tissue. Here, one notch of the pair of spaced notches is defined in each respective elongate edge of the body. Further, each notch may have a keyhole shape. In another example shown in FIG. 4C, the body has at least a pair of spaced bores 120 extending between the upper and lower surfaces of the body. As one will appreciate, a suture can be passed through the bores for subsequent securing to the sclera. To simplify the surgical procedure, at least one suture may be preloaded into the stitching loop, notches, bores, and the like of the device prior to inserting the device into the eye.

The device of the present invention is designed to be implanted through an incision or cleft formed in the anterior chamber angle of the eye by the shearing edge of the shunt 10. Because of the simplicity of the insertion of the device and the similarities to the traditional cyclodialysis procedure, the method and device should be readily accepted by general ophthalmologists who can incorporate the use of the implant easily into already established surgical techniques. It would thus present an attractive and cost effective technological alternative for an eye surgeon. Because the procedure can be done quickly with minimum instrumentation, the device of the present invention would be especially advantageous in developing nations, where glaucoma is a leading cause of blindness.

Turning now to FIGS. 6A–7B, the surgical method for implanting the device of the present invention into an eye will be explained. A first incision or slit is made through the conjunctiva and the sclera at a location rearward of the limbus, that is, posterior to the region of the sclera at which the opaque white sclera starts to become clear cornea. Preferably, the first incision is made about 3 mm posterior to the limbus. Also, the first incision is made slightly larger than the width of the implant device. A conventional cyclodialysis spatula may be inserted through the first incision into the supraciliary space to confirm correct anatomic position.

A portion of the upper and lower surfaces of the shunt 10 proximate the back end of the body is then grasped securely by the surgical tool, for example, a forceps, so that the forward end of the shunt is oriented properly. In one example, the shunt is oriented with the longitudinal axis of the device being substantially co-axial to the longitudinal axis of the grasping end of the surgical tool. The shunt 10 is then disposed through the first incision and into the supraciliary space of the eye. The shearing edge of the shunt is advanced anteriorly in the supraciliary space and is inserted into and through the anterior chamber angle of the eye. More particularly, the shearing edge of the insertion head passes preferably between the scleral spur and the ciliary body posterior to the trabecular meshwork. The shunt is continually advanced anteriorly until a portion of the insertion head and the first end of the conduit is disposed within the anterior chamber of the eye. Thus, the first end of the conduit is placed into fluid communication with the anterior chamber of the eye. The back end of the elongate body is disposed into the suprachoroidal space of the eye so that the second end of the conduit is placed into fluid communication with the suprachoroidal space.

The shoulder surface of the forward end of the shunt is seated proximate an interior surface of the supraciliary space and is not introduced into the anterior chamber. The shoulder surface aids in forming a tight seal to prevent leakage of aqueous humor around the device as well as helping to prevent unwanted further anterior movement of the shunt. The shape of the cleft formed by the insertion head forms a tight seal about the exterior surface of the body, and, if used, the fusiform cross-sectional shape of the body prevents gaping of the formed cleft on either elongate edge of the shunt.

The shunt is then sutured to a portion of the sclera to aid in fixating the shunt. The first incision is subsequently sutured closed. As one will appreciate, the suture used to fixate the shunt may also be used to close the first incision.

It will be seen that upon implantation, the drainage device forms a cyclodialysis with the conduit providing transverse communication of aqueous humor through the shunt along its length. Aqueous humor thus delivered to the suprachoroidal space will then be absorbed therein, and additional reduction in pressure within the eye is to be expected.

The device may be made from any biological inert and biocompatible materials having the desired characteristics. The elongate body may be substantially rigid or may be substantially resilient and semi-rigid. Further, the exterior surface of the elongate body is non-porous. Various medically suitable acrylics and other plastics are considered appropriate. The finish of the device should be to the standard for ophthalmic devices and should not created irritation to surrounding tissue. In one example, the device may be made by conventional liquid injection molding or transfer molding process.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. An ophthalmic shunt implantable in an eye, comprising:

an elongate body having a forward end, a spaced back end, and an insertion head extending from the forward end of the elongate body, the insertion head having a top surface and defining a shearing edge constructed and arranged for cutting eye tissue engaged thereby, the body having a substantially fusiform cross-sectional shape, the forward end and the insertion head of said body further defining a shoulder surface; and a tubular enclosed conduit having a first end defined on a portion of the top surface of said insertion head and extending through said body from the forward end to the back end thereof, the first end being spaced from the shearing edge and the shoulder surface of said body, wherein the elongate body is configured to position at least a portion of the insertion head and the first end of the conduit through an incision formed by the shearing edge of the insertion head and into fluid communication with the anterior chamber of the eye and to seat at least a portion of the shoulder surface of the insertion head against the incision to seal the incision.

2. The shunt of claim 1, wherein the elongate body has a lower surface, and wherein a portion of the insertion head is substantially co-planar to the lower surface thereof.

3. The shunt of claim 1, wherein the elongate body has an arcuate shape along at least a portion of its length that is adapted to extend along the curvature of the sclera.

4. The shunt of claim 1, wherein the elongate body has an upper surface and a spaced lower surface, and wherein at lease one planar surface, configured to be grasped by a surgical tool, is defined on at least a portion of at least one of the respective upper and lower surfaces of the elongate body.

5. The shunt of claim 1, wherein the elongate body has a longitudinal axis, and wherein a longitudinally extending groove, configured to be grasped by a surgical tool, is defined on at least a portion of an exterior surface of the elongate body.

6. The shunt of claim 5, wherein the elongate body has an upper surface and a spaced lower surface, and wherein the longitudinally extending groove is defined on at least a portion of the upper surface of the elongate body.

7. The shunt of claim 6, wherein a planar surface, configured to be grasped by the surgical tool, is defined on at least a portion of the lower surface of the elongate body.

8. The shunt of claim 6, wherein a second longitudinally extending groove, configured to be grasped by the surgical tool, is defined on at least a portion of the lower surface of the elongate body.

9. The shunt of claim 1, wherein the first end of the conduit is positioned at an acute angle with respect to the top surface of the insertion head.

10. The shunt of claim 1, wherein the elongate body is substantially rigid.

11. The shunt of claim 1, wherein the elongate body is comprised of biocompatible materials.

12. The shunt of claim 1, wherein an exterior surface of the elongate body is non-porous.

13. The shunt of claim 1, wherein the elongate body has a first elongate edge and a spaced second elongate edge, and wherein said body has at least a pair of spaced notches bores configured to facilitate suturing the elongate body to eye tissue, one notch of the pair of spaced notches being defined in each respective elongate edge.

14. The shunt of claim 1, wherein the elongate body has an upper surface and a spaced lower surface, and wherein the body has at least a pair of spaced bores extending between the upper and lower surfaces of said body, the pair of spaced bores configured to facilitate suturing the elongate body to eye tissue.

15. The shunt of claim 1, wherein the conduit comprises a wicking member configured to regulate the flow of aqueous humor from an inlet end to an outlet end of the wicking member.

16. The shunt of claim 1, further comprising a wicking member configured to regulate the flow of aqueous humor from an inlet end to an outlet end of the wicking member, the wicking member disposed within at least a portion of the conduit.

17. The shunt of claim 1, further comprising a means for regulating the flow of aqueous humor from the first end of the conduit to the back end thereof.

18. An ophthalmic shunt implantable in an eye, comprising:
a thin elongate body of a biocompatible material, the body having a forward end, a spaced back end, and a substantially fusiform cross-sectional shape, said body further comprising an insertion head extending from the forward end of the elongate body, the insertion head having a top surface and defining a shearing edge constructed and arranged for cutting eye tissue engaged thereby, the shearing edge having a substantially arcuate shape, the forward end and the insertion head of said body further defining a shoulder surface; and a tubular enclosed conduit defined on a portion of the top surface of said insertion head and extending through said body from the forward end to the back end thereof, the conduit having a first end that is spaced from the shearing edge, wherein the elongate body is configured to position at least a portion of the insertion head and the first end of the conduit through an incision formed by the shearing edge of the insertion head and into fluid communication with the anterior chamber of the eye and to seat at least a portion of the shoulder surface of the insertion head against the incision to seal the incision.

19. The shunt of claim 18, wherein the insertion head has a base portion having a first width, wherein the elongate body has a first elongate edge and a spaced second elongate edge, and wherein the first and second elongate edges are spaced a second width that is greater than said first width.

20. The shunt of claim 18, wherein the elongate body has a lower surface, and wherein a portion of the insertion head is substantially co-planar to the lower surface thereof.

21. The shunt of claim 18, wherein the elongate body has an arcuate shape along at least a portion of its length that is adapted to extend along the curvature of the sclera.

22. The shunt of claim 18, wherein the elongate body has an upper surface and a spaced lower surface, and wherein at least one planar surface, configured to be grasped by a surgical tool, is defined on at least a portion of at least one of the respective upper and lower surfaces of the elongate body.

23. The shunt of claim 18, wherein the elongate body has a longitudinal axis, and wherein a longitudinally extending groove, configured to be grasped by a surgical tool, is defined on at least a portion of an exterior surface of the elongate body.

24. The shunt of claim 23, wherein the elongate body has an upper surface and a spaced lower surface, and wherein the longitudinally extending groove is defined on at least a portion of the upper surface of the elongate body.

25. The shunt of claim 24, wherein a planar surface, configured to be grasped by a surgical tool, is defined on at least a portion of the lower surface of the elongate body.

26. The shunt of claim 24, wherein a second longitudinally extending groove is defined on at least a portion of the lower surface of the elongate body.

27. The shunt of claim 18, wherein an exterior surface of the elongate body is non-porous.

28. The shunt of claim 18, wherein the elongate body has a first elongate edge and a spaced second elongate edge, and wherein said body has at least a pair of spaced notches configured to facilitate suturing the elongate body to eye tissue, one notch of the pair of spaced notches being defined in each respective elongate edge.

29. The shunt of claim 18, wherein the elongate body has an upper surface and a spaced lower surface, and wherein the body has at least a pair of spaced bores extending between the upper and lower surfaces of said body, the pair of spaced bores configured to facilitate suturing the elongate body to eye tissue.

30. The shunt of claim 18, wherein the elongate body has a length of such extent to extend from proximate the anterior chamber of the eye to the suprachoroidal space.

31. The shunt of claim 18, wherein the conduit comprises a wicking member configured to regulate the flow of aqueous humor from an inlet end to an outlet end of the wicking member.

32. The shunt of claim 18, further comprising a wicking member configured to regulate the flow of aqueous humor from an inlet end to an outlet end of the wicking member, the wicking member disposed within at least a portion of the conduit.

33. The shunt of claim 18, further comprising a means for regulating the flow of aqueous humor from the first end of the conduit to the back end thereof.

34. An ophthalmic shunt implantable in an eye, comprising:
   a thin elongate body of biocompatible material, the body having a longitudinal axis, a forward end, a spaced back end, and a substantially fusiform cross-sectional shape, the body further comprising an insertion head extending from the forward end of the elongate body, the insertion head having a top surface and defining a shearing edge constructed and arranged for cutting eye tissue engaged thereby, the body defining a longitudinally extending bore, a proximal end of the bore defined in the forward end of the body, the proximal end positioned adjacent a portion of the top surface of the insertion head, the forward end and the insertion head of said body further defining a shoulder surface; and
   a tube of biocompatible material, the tube having a first end and a spaced second end, at least a portion of the tube positioned within the bore of said body such that the second end of the tube is adjacent a distal end of the bore of said body and such that the first end of the tube extends through the proximal end of the bore and overlies a portion of the top surface of the insertion head, the first end of the tube being spaced from the shearing edge and the shoulder surface of said body,
   wherein the elongate body is configured to position at least a portion of the insertion head and the first end of the tube through an incision formed by the shearing edge of the insertion head and into fluid communication with the anterior chamber of the eye and to seat at least a portion of the shoulder surface of the insertion head against the incision to seal the incision.

35. The shunt of claim 34, wherein the shearing edge has a substantially arcuate shape.

36. The shunt of claim 34, further comprising a means for regulating the flow of aqueous humor from the first end of the conduit to the back end thereof.

37. An ophthalmic shunt implantable in an eye, comprising:
   a thin elongate body of biocompatible material, the body having a longitudinal axis, an upper surface, a forward end, a spaced back end, and an insertion head extending from the forward end of the elongate body, the insertion head having a top surface and defining a shearing edge constructed and arranged for cutting eye tissue engaged thereby, the upper surface of the body defining a longitudinally extending slit, the forward end and the insertion head of said body further defining a shoulder surface; and
   a wicking member having an inlet end and an outlet end, the wicking member configured to regulate the flow of aqueous humor from the inlet end to the outlet end and for positioning within at least a portion of the slit of said body and overlying a portion of the top surface of the insertion head, the inlet end of the wicking member being spaced from the shearing edge of said body,
   wherein the elongate body is configured to position at least a portion of the insertion head and the inlet end of the wicking member through an incision formed by the shearing edge of the insertion head and into fluid communication with the anterior chamber of the eye and to seat at least a portion of the shoulder surface of the insertion head against the incision to seal the incision.

38. The shunt of claim 37, wherein the shearing edge has a substantially arcuate shape.

39. The shunt of claim 37, wherein the body has a substantially fusiform cross-sectional shape.

40. The shunt of claim 37, wherein the elongate body has a lower surface, and wherein at least one planar surface, configured to be grasped by a surgical tool, is defined on at least a portion of at least one of the respective upper and lower surfaces of the elongate body.

41. The shunt of claim 37, wherein one planar surface is defined in a portion of the slit of said body.

42. The shunt of claim 37, wherein the elongate body has a longitudinal axis, and wherein a longitudinally extending groove, configured to be grasped by a surgical tool, is defined on at least a portion of an exterior surface of the elongate body.

43. The shunt of claim 37, wherein an exterior surface of the elongate body is non-porous.

44. The shunt of claim 37, wherein the elongate body has a first elongate edge and a spaced second elongate edge, and wherein said body has at least a pair of spaced notches configured to facilitate suturing the elongate body to eye tissue, one notch of the pair of spaced notches being defined in each respective elongate edge.

45. The shunt of claim 37, wherein the elongate body has a lower surface, and wherein the body has at least a pair of spaced bores extending between the upper and lower surfaces of said body, the pair of spaced bores configured to facilitate suturing the elongate body to eye tissue.

46. The shunt of claim 37, wherein the elongate body has a length of such extent to extend from proximate the anterior chamber of the eye to the suprachoroidal space.

47. A method for lowering eye pressure in an eye, comprising:
   a. making a first incision in and through the conjunctiva and the sclera at a position posterior to the limbus;
   b. providing a biocompatible ophthalmic shunt comprising:
      i. an elongate body having a forward end, a spaced back end, and an insertion head extending from the forward end of the elongate body, the insertion head having a top surface and defining a shearing edge constructed and arranged for cutting eye tissue engaged thereby, the forward end and the insertion head of said body defining a shoulder surface; and
      ii. a tubular enclosed conduit having a first end defined on a portion of the top surface of said insertion head and extending through said body from the forward end to the back end thereof, the first end being spaced from the shearing edge and the shoulder surface of said body, wherein the elongate body is configured to position at least a portion of the insertion head and the first end of the conduit through an incision formed by the shearing edge of the insertion head and into fluid communication with the anterior chamber of the eye and to seat at least a portion of the shoulder surface of the insertion head against the incision to seal the incision;

c. grasping a portion of the elongate body of the shunt;

d. disposing the insertion head of the shunt in and through the first incision and into the supracilliary space of the eye;

e. inserting at least a portion of the shearing edge of the insertion head of the shunt into and through the anterior chamber angle and into the anterior chamber of the eye so that the first end of the conduit is in fluid communication with the anterior chamber;

f. forcing the insertion head anteriorally to seat the shoulder surface of the implant adjacent an interior surface of the supraciliary space of the eye; and g. suturing the first incision closed.

48. The method of claim 47, further comprising suturing the implant to a portion of the sclera.

49. A method for treating glaucoma in an eye, comprising:

a. providing a biocompatible ophthalmic shunt comprising:

i. a thin elongate body of a biocompatible material, the body having a forward end, a spaced back end, and a substantially fusiform cross-sectional shape, said body further comprising an insertion head extending from the forward end of the elongate body, the insertion head having a top surface and defining a shearing edge constructed and arranged for cutting eye tissue engaged thereby, the shearing edge having a substantially arcuate shape, the forward end and the insertion head of said body defining a shoulder surface; and ii. a tubular enclosed conduit defined on a portion of the top surface of said insertion head and extending through said body from the forward end to the back end thereof, the conduit having a first end that is spaced from the shearing edge and the shoulder surface of said body, wherein the elongate body is configured to position at least a portion of the insertion head and the first end of the conduit through an incision formed by the shearing edge of the insertion head and into fluid communication with the anterior chamber of the eye and to seat at least a portion of the shoulder surface of the insertion head against the incision to seal the incision;

b. inserting at least a portion of the shearing edge of the insertion head of the shunt into and through the anterior chamber angle and into the anterior chamber of the eye;

c. disposing the first end of the conduit into fluid communication with the anterior chamber of the eye;

d. introducing the insertion head anteriorally to seat the shoulder surface of the implant adjacent an interior surface of the supraciliary space of the eye;

e. disposing the back end of the elongate body of the shunt into the suprachoroidal space of the eye so that a second end of the conduit is in fluid communication with the suprachoroidal space; and f. securing the shunt to the eye by suturing a portion of the elongate body to the eye.

50. The method of claim 49, wherein the shunt is sutured to a portion of the sclera.

51. The method of claim 49, further comprising, prior to the insertion of the insertion head into the anterior chamber making a first incision in and through the conjunctiva and the sclera at a position posterior to the limbus.

52. An ophthalmic shunt implantable in an eye, comprising:

an elongate body having a forward end, a spaced back end, and an insertion head extending from the forward end of the elongate body, the insertion head defining a shearing edge constructed and arranged for cutting eye tissue engaged thereby, the forward end and the insertion head of said body further defining a shoulder surface; and a tubular enclosed conduit having a first end defined on a portion of the insertion head and extending through said body from the forward end to the back end thereof, the first end of the conduit being spaced from the shearing edge and the shoulder surface of said body, wherein the elongate body is configured to position at least a portion of the insertion head and the first end of the conduit through an incision formed by the shearing edge of the insertion head and into fluid communication with the anterior chamber of the eye and to seat at least a portion of the shoulder surface of the insertion head against the incision to seal the incision.

53. The shunt of claim 52, further comprising a means for regulating the flow of aqueous humor from the first end of the conduit to the back end thereof.

54. The shunt of claim 52, further comprising a means for grasping the elongate body.

55. The shunt of claim 52, further comprising a means for facilitating suturing the elongate body to eye tissue.

56. The shunt of claim 52, wherein the elongate body is substantially rigid.

57. The shunt of claim 52, wherein the elongate body is comprised of biocompatible materials.

58. The shunt of claim 52, wherein the insertion head has a base portion having a first width, wherein the elongate body has a first elongate edge and a spaced second elongate edge, and wherein the first and second elongate edges are spaced a second width that is greater than said first width.

59. The shunt of claim 52, wherein the elongate body has a lower surface, and wherein a portion of the insertion head is substantially co-planar to the lower surface thereof.

60. The shunt of claim 52, wherein the elongate body has an arcuate shape along at least a portion of its length that is adapted to extend along the curvature of the sclera.

61. The shunt of claim 52, wherein the elongate body has a length of such extent to extend from proximate the anterior chamber of the eye to proximate the suprachoroidal space.

62. The shunt of claim 52, wherein the body has a substantially fusiform cross-sectional shape.

63. An ophthalmic shunt implantable in an eye, comprising:

an elongate body of a biocompatible material, the body having a forward end, a spaced back end, said body further comprising an insertion head extending from the forward end of the elongate body, the insertion head defining a shearing edge constructed and arranged for cutting eye tissue engaged thereby, the shearing edge having a substantially arcuate shape, the forward end and the insertion head of said body further defining a shoulder surface; and a tubular enclosed conduit defined on a portion of the insertion head and extending through said body from the forward end to the back end thereof, the conduit having a first end that is spaced from the shearing edge, wherein the elongate body is configured to position at least a portion of the insertion head and the first end of the conduit through an incision formed by the shearing edge of the insertion head and into fluid communication with the anterior chamber of the eye and to seat at least a portion of the shoulder surface of the insertion head against the incision to seal the incision.

64. The shunt of claim 63, further comprising a means for regulating the flow of aqueous humor from the first end of the conduit to the back end thereof.

65. The shunt of claim 63, further comprising a means for grasping the elongate body.

66. The shunt of claim 63, further comprising a means for facilitating suturing the elongate body to eye tissue.

67. The shunt of claim 63, wherein the elongate body is substantially rigid.

68. The shunt of claim 63, wherein the elongate body is comprised of biocompatible materials.

69. The shunt of claim 63, wherein the insertion head has a base portion having a first width, wherein the elongate body has a first elongate edge and a spaced second elongate edge, and wherein the first and second elongate edges are spaced a second width that is greater than said first width.

70. The shunt of claim 63, wherein the elongate body has a lower surface, and wherein a portion of the insertion head is substantially co-planar to the lower surface thereof.

71. The shunt of claim 63, wherein the elongate body has an arcuate shape along at least a portion of its length that is adapted to extend along the curvature of the sclera.

72. The shunt of claim 63, wherein the elongate body has a length of such extent to extend from proximate the anterior chamber of the eye to proximate the suprachoroidal space.

73. The shunt of claim 63, wherein the body has a substantially fusiform cross-sectional shape.

74. An ophthalmic shunt implantable in an eye, comprising:
  an elongate body of biocompatible material, the body having a longitudinal axis, a forward end, a spaced back end, the body further comprising an insertion head extending from the forward end of the elongate body, the insertion head defining a shearing edge constructed and arranged for cutting eye tissue engaged thereby, the body defining a longitudinally extending bore, a proximal end of the bore defined in the forward end of the body, the proximal end positioned adjacent a portion of a surface of the insertion head, the forward end and the insertion head of said body further defining a shoulder surface; and
  a tube of biocompatible material, the tube having a first end and a spaced second end, at least a portion of the tube positioned within the bore of said body such that the second end of the tube is adjacent a distal end of the bore of said body and such that the first end of the tube extends through the proximal end of the bore and overlies a portion of the surface of the insertion head, the first end of the tube being spaced from the shearing edge and the shoulder surface of said body,
  wherein the elongate body is configured to position at least a portion of the insertion head and the first end of the tube through an incision formed by the shearing edge of the insertion head and into fluid communication with the anterior chamber of the eye and to seat at least a portion of the shoulder surface of the insertion head against the incision to seal the incision.

75. The shunt of claim 74, further comprising a means for regulating the flow of aqueous humor from the first end of the conduit to the back end thereof.

76. The shunt of claim 74, further comprising a means for grasping the elongate body.

77. The shunt of claim 74, further comprising a means for facilitating suturing the elongate body to eye tissue.

78. The shunt of claim 74, wherein the elongate body is substantially rigid.

79. The shunt of claim 74, wherein the elongate body is comprised of biocompatible materials.

80. The shunt of claim 74, wherein the insertion head has a base portion having a first width, wherein the elongate body has a first elongate edge and a spaced second elongate edge, and wherein the first and second elongate edges are spaced a second width that is greater than said first width.

81. The shunt of claim 74, wherein the elongate body has a lower surface, and wherein a portion of the insertion head is substantially co-planar to the lower surface thereof.

82. The shunt of claim 74, wherein the elongate body has an arcuate shape along at least a portion of its length that is adapted to extend along the curvature of the sclera.

83. The shunt of claim 74, wherein the elongate body has a length of such extent to extend from proximate the anterior chamber of the eye to proximate the suprachoroidal space.

84. The shunt of claim 74, wherein the body has a substantially fusiform cross-sectional shape.

* * * * *